United States Patent
Fiorenza

(10) Patent No.: US 10,350,377 B2
(45) Date of Patent: Jul. 16, 2019

(54) BYPASS SYSTEM AND METHOD FOR RESPIRATORY THERAPY AND ANESTHESIA

(71) Applicant: Francesco Fiorenza, Ottawa (CA)

(72) Inventor: Francesco Fiorenza, Ottawa (CA)

(73) Assignee: Smart RS Inc., Ottawa (CA)

( * ) Notice: Subject to any disclaimer, the term of this patent is extended or adjusted under 35 U.S.C. 154(b) by 646 days.

(21) Appl. No.: 14/603,662

(22) Filed: Jan. 23, 2015

(65) Prior Publication Data

US 2015/0202398 A1 Jul. 23, 2015

Related U.S. Application Data

(60) Provisional application No. 61/930,760, filed on Jan. 23, 2014.

(51) Int. Cl.
| | | |
|---|---|---|
| *A61M 16/00* | (2006.01) | |
| *A61M 16/08* | (2006.01) | |
| *F17D 5/00* | (2006.01) | |
| *A61M 16/10* | (2006.01) | |
| *A61M 16/20* | (2006.01) | |

(52) U.S. Cl.
CPC ......... *A61M 16/0875* (2013.01); *F17D 5/005* (2013.01); *A61M 16/104* (2013.01); *A61M 16/105* (2013.01); *A61M 16/1045* (2013.01); *A61M 16/201* (2014.02); *A61M 2205/7581* (2013.01); *Y10T 137/794* (2015.04)

(58) Field of Classification Search
CPC .. A61M 16/00; A61M 16/01; A61M 16/0816; A61M 16/1045; A61M 16/16; A61M 16/164; A61M 16/0087–0093; A61M 16/9463–047; A61M 16/0808; A61M 16/0875; A61M 16/0833; A61M 16/0891; A61M 16/104; A61M 16/105–107; A61M 16/1075; A61M 16/1095; A61M 16/208; A61M 16/22; A61M 9/203; Y10S 165/092; Y10S 165/109
USPC ....................................................... 251/149.2
See application file for complete search history.

(56) References Cited

U.S. PATENT DOCUMENTS

| | | | | |
|---|---|---|---|---|
| 5,421,813 A * | 6/1995 | Ohnishi | .............. | A61M 1/3643 137/599.14 |
| 6,152,133 A * | 11/2000 | Psaros | .................. | A61M 16/009 128/203.12 |
| 6,588,421 B1 * | 7/2003 | Diehl | ..................... | A61M 16/12 128/201.13 |
| 2008/0127976 A1* | 6/2008 | Acker | .................... | A61M 16/08 128/204.18 |
| 2009/0301477 A1* | 12/2009 | Pierro | ............... | A61M 16/1045 128/201.13 |

(Continued)

*Primary Examiner* — Steven O Douglas
(74) *Attorney, Agent, or Firm* — Timothy D. Bennett; Emerson Thomson Bennett

(57) ABSTRACT

A bypass system for respiratory therapy and anaesthesia having a first bypass conduit for receiving a gas flow and for receiving a filtration device. The bypass system also has an activation device for redirecting the gas flow within the first bypass conduit. A second bypass conduit is also present in the bypass system which has a passive control valve to redirect air flow within the second bypass conduit. A conduit interconnects the first and second bypass conduit for providing a passage of gases between the first and second bypass conduits.

9 Claims, 14 Drawing Sheets

(56) References Cited

U.S. PATENT DOCUMENTS

| | | | |
|---|---|---|---|
| 2012/0000549 A1* | 1/2012 | Thorne | A61M 16/01 137/455 |
| 2013/0199524 A1* | 8/2013 | Hardin | A61M 16/0816 128/202.27 |

* cited by examiner

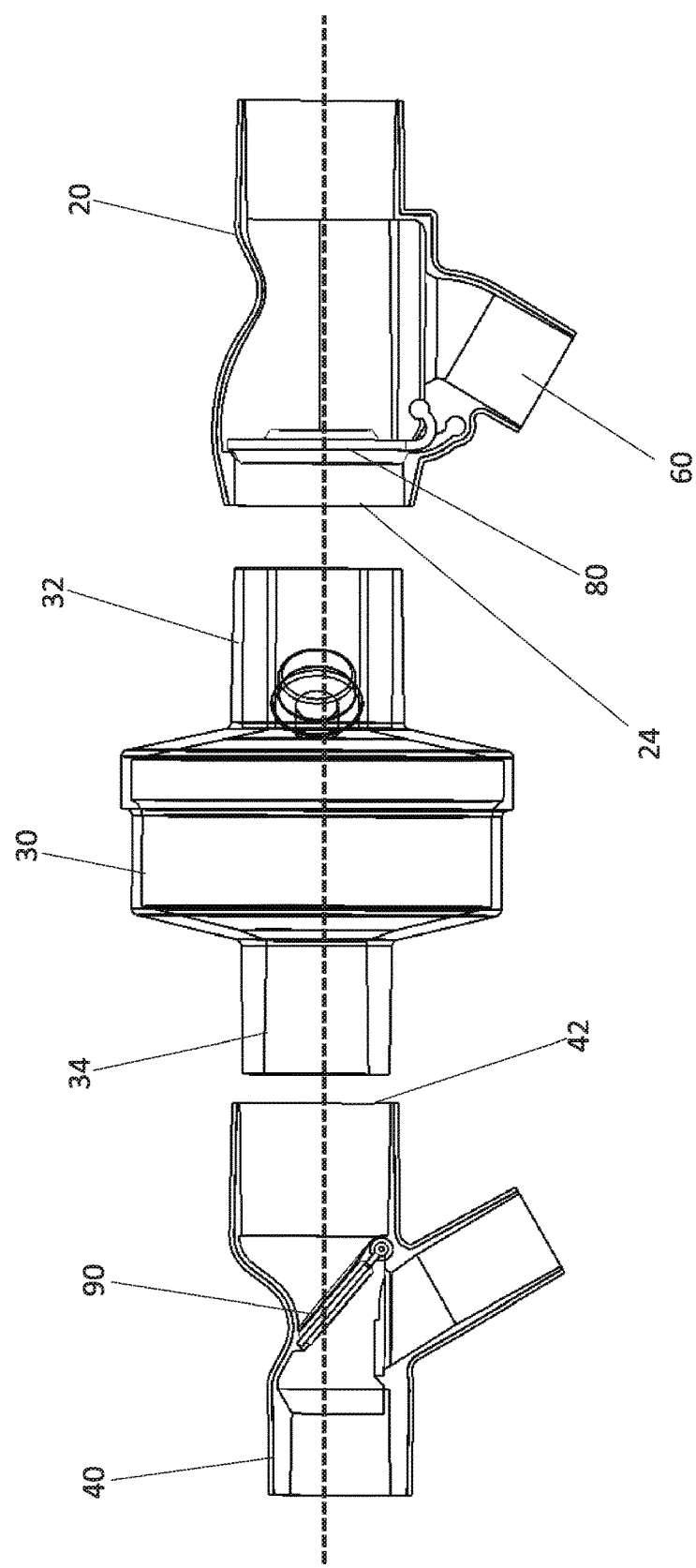

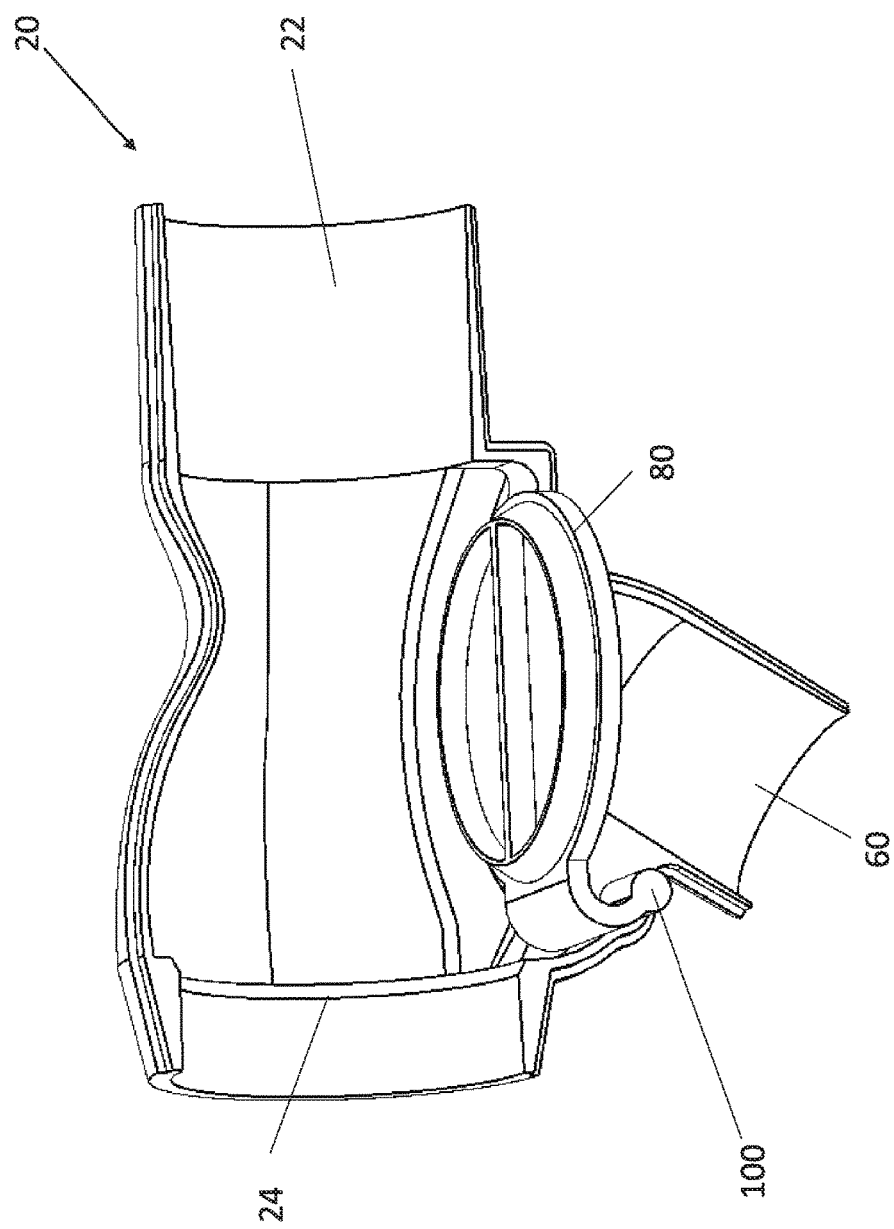

BYPASS SYSTEM AND METHOD FOR RESPIRATORY THERAPY AND ANESTHESIA

CROSS-REFERENCE TO RELATED APPLICATION

This application claims priority from U.S. Provisional Patent Application No. 61/930,760, entitled BYPASS SYSTEM AND METHOD FOR RESPIRATORY THERAPY AND ANAESTHESIA, filed Jan. 23, 2014, which is incorporated herein by reference.

FIELD OF THE INVENTION

The present invention relates to artificial ventilation used in respiratory therapy and anesthesia devices and, in particular, to a single patient use bypass for providing an uninterrupted flow air/oxygen during the removal or replacement of components within an artificial ventilation system.

BACKGROUND OF THE INVENTION

As is known to those in the respiratory care field, HME's are humidifying filters which are frequently used in medical procedures, for example in mechanical ventilator circuits such as when intubating patients, to prevent deterioration of respiratory functions. These devices capture heat and moisture on expiration, and return it to the patient on inspiration. After a certain period of usage, the HME requires to be changed in order to maintain proper functionality of the HME. During the procedure of removing or replacing the HME, the flow of air is interrupted which allows for possible contaminants or germs to enter into the patient, as well as the loss of positive end expiratory pressure (PEEP), which is not a desired result.

Various HME units have been suggested that incorporate intricate bypass structures/valves that selectively and completely isolate the HME media from the airflow path. For example, existing bypass-type HME units employ a bypass structure that is internal or through the HME media. While viable, these and other bypass-type HME units are difficult to operate (e.g., requiring a caregiver to rotate two frictionally fitting housing units relatively to each other) and/or are relatively complex and thus expensive.

In addition, while the HME unit addresses the heat and humidity concerns associated with ventilator-provided air in the breathing circuit, other drawbacks may exist. For example, it is fairly common to introduce aerosolized medication particles into the breathing circuit (e.g., via a nebulizer or metered dose inhaler) for delivery to the patient's lungs. However, where an HME unit is present in the breathing circuit, the medication particles will not readily traverse the HME media and thus not be delivered to the patient. This invention can also be used to administer inhaled medications through the bypass tubing to avoid the HME media through the use of a commonly found adapter allowing the administration of inhaled medications.

Furthermore, the HME media can become clogged with the droplets of liquid medication, in some instances leading to an elevated resistance of the HME unit. One approach for addressing these concerns is to remove the HME unit from the breathing circuit when introducing aerosolized medication. This step is time consuming, subject to errors and can result in the loss of recruited alveoli when the circuit is depressurized alongside opening the patient circuit which puts them at risk of infection from bacteria or viruses from entering into the circuit.

In light of the above, a need exists for a standalone device having an HME media bypass feature that addresses one or more of the problems associated with conventional bypass-type HME units. In certain of such usages it is also necessary to administer medication to the patient in the form of a mist or fine spray which is inhaled by the patient.

Accordingly, it would be highly beneficial and much more efficient if the HME could be removed and the flow of air would be automatically diverted into a bypass conduit allowing for the respiratory system to continue functioning without any interruption. It would also be highly beneficial for the flow of air to be returned through the HME once the HME is re-introduced into the respiratory system without the need to operate or control any bypass valves.

SUMMARY OF THE INVENTION

The present invention provides a bypass system for respiratory therapy and anesthesia.

In a first aspect of the present invention, the present invention provides a bypass system for respiratory therapy and anesthesia comprising a first bypass conduit for receiving a gas flow and for receiving a filtration device. An activation means for redirecting the gas flow within the first bypass conduit. A second bypass conduit for receiving the gas flow from a first bypass conduit and a filtration device. A passive control valve within the second bypass conduit to redirect air flow within the second bypass conduit and a conduit interconnected to the first and second bypass conduit for providing a passage of gases between the first and second bypass conduit when activated by the activation means wherein the activation means is activated when the first bypass conduit is not connected to a filtration device.

In a second aspect, the present invention also provides a method for bypassing air flow for use in respiratory therapy and anesthesia comprising the steps of a) providing an air flow passage to a patient for assistance in artificial ventilation having an air flow passage; b) disconnecting a first bypass conduit from the air flow passage; and c) diverting the air flow into a conduit interconnecting the first bypass conduit and a second bypass conduit.

BRIEF DESCRIPTION OF THE DRAWINGS

The embodiments of the present invention will now be described by reference to the following figures, in which identical reference numerals in different figures indicate identical elements and in which:

FIG. 4 is another cross section view of the first and second bypass conduits unconnected to a heat and moisture exchanger;

FIG. 5a is a vertical plane cross-sectional view of the first bypass conduit with a first control valve in a closed position;

The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention.

DETAILED DESCRIPTION OF THE INVENTION

The terms "coupled" and "connected", along with their derivatives, may be used herein. It should be understood that these terms are not intended as synonyms for each other. Rather, in particular embodiments, "connected" may be used to indicate that two or more elements are in direct physical or electrical contact with each other. "Coupled" may be used to indicated that two or more elements are in either direct or indirect (with other intervening elements between them) physical or electrical contact with each other, or that the two or more elements co-operate or interact with each other (e.g. as in a cause and effect relationship).

The term gas as used in this application can include oxygen, air, heliox, nitric oxide, anesthetic agents or a combination thereof and as would be known by a worker skilled in the relevant art.

Figure 1:
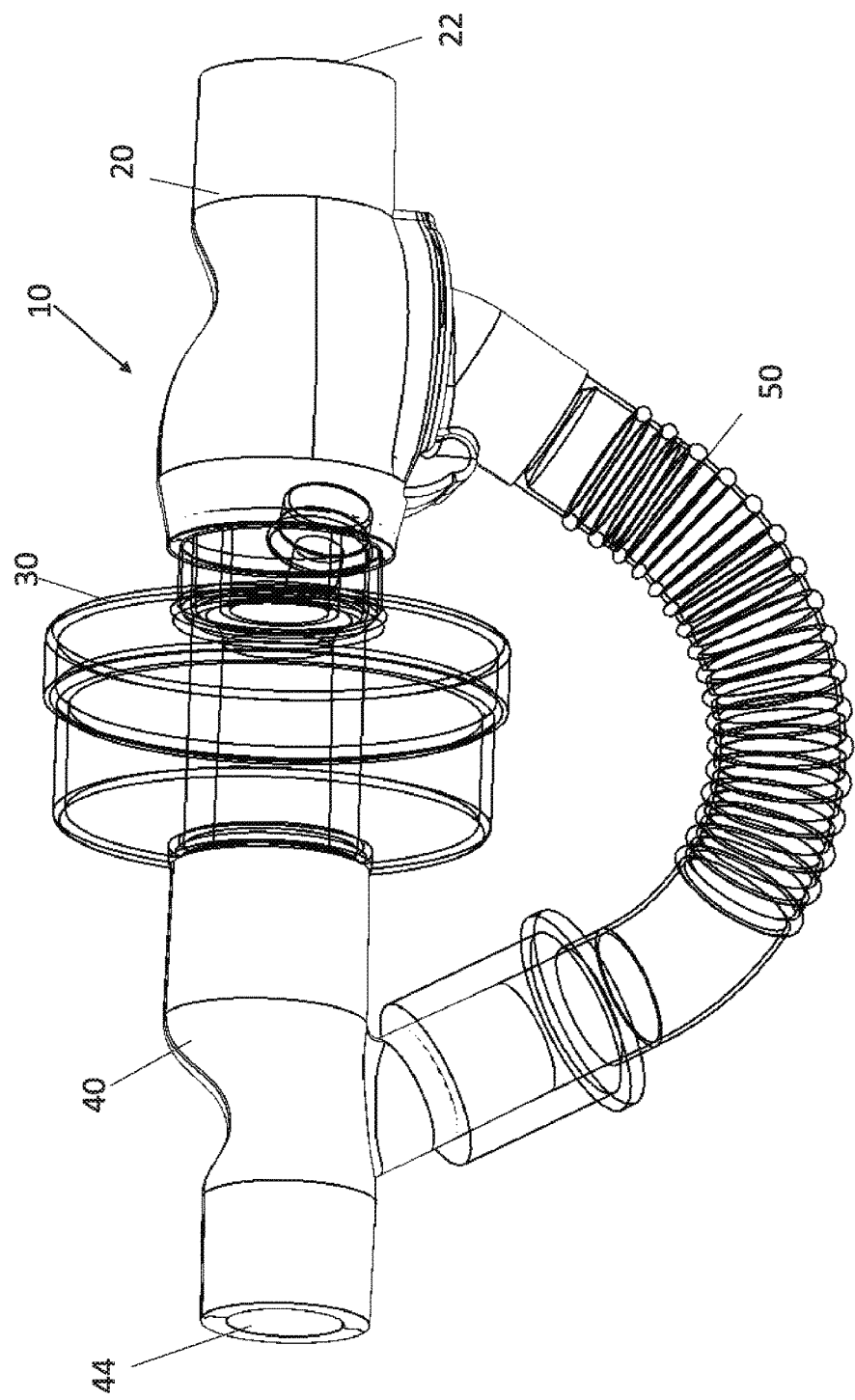
FIG. 1 is a perspective view of a bypass system for respiratory therapy and anesthesia of the present invention installed on a heat and moisture exchanger according to one embodiment of the present invention.

With reference to FIG. 1 and according to one embodiment of the present invention, a bypass system for respiratory therapy 10 is shown having a first bypass conduit 20 connected to a filtration device at one end. In one embodiment of the present invention and as shown in FIG. 1, the filtration device can be a heat and moisture exchanger (HME) 30, or any other filtration mechanism known to a worker skilled in the relevant art, inclusive of a connecting conduit as described herein. At the opposite of the HME 30 a second bypass conduit 40 is attached to the HME 30. In normal operation, the air flow travels initially through the first bypass conduit 20, through the HME 30 and then through the second bypass conduit 40 to reach a patient not shown. The HME 30 used in this system is a commonly used HME as would be found in this field of respiratory therapy and as would be known by a worker skilled in the relevant art. The first and second bypass conduits 20 and 40 can be easily designed to connect with any commonly available HME 30 as would be known by a worker skilled in the relevant. A worker skilled in the relevant art would be familiar with the ability of the first and second bypass conduits 20 and 40 to be fitted to the inner or outer diameter of the HME conduits as commonly found on an HME. The most common connection device would be a press fit or any other connecting device as would be known by a worker skilled in the relevant art. The first and second bypass conduits 20 and 40 have conduits (not shown) connected to their respective opposite ends not connected to the HME 30. The first bypass conduit 20 has an aperture 22 and second conduit 40 has aperture 44. When such conduits are connected to the first and second bypass conduits 20 and 40, a closed circuit under a specific pressure is created (dependant on the settings of the mechanical ventilator or anaesthesia machine set by the health care professional). When the first bypass conduit 20 is removed from an HME 30, for example, this causes the pressure in the HME 30 to drop to atmosphere. Activation means then redirects the flow through conduit 20 by an automatic activation of the first bypass control valve to the second bypass conduit 40 through conduit 50. When an HME is reconnected or a humidity adapter conduit (not shown), the activation means closes the first bypass valve and the pressure is greater through the main channel which closes the passive valve (not shown) in the second conduit 40. The operation of the valves within the first and second bypass conduits 20 and 40 are further described below.

With further reference to FIG. 1, the first and second bypass conduits 20 and 40 are interconnected through the use of a conduit 50. The conduit 50 is a commonly used conduit as would be used in the field of respiratory therapy and as would be known by a worker skilled in the relevant art. The conduit 50 is an example of an interconnecting means in order to interconnect the first and second bypass conduits 20 and 40 of the present system without the use of an HME 30 or a humidity adapter conduit (not shown). To ensure optimal function of the system, the conduit should be flexible and have a length ranging from 3 inches to 6 inches or a range of 30 cc to 60 cc in internal volume should be used. The conduit 50 has to be able to interconnect bypass conduits 20 and 40 and provide an airtight seal in order to reduce the possibility of germs from penetrating into the system while providing respiratory therapy or anesthesia for example.

Figure 2:
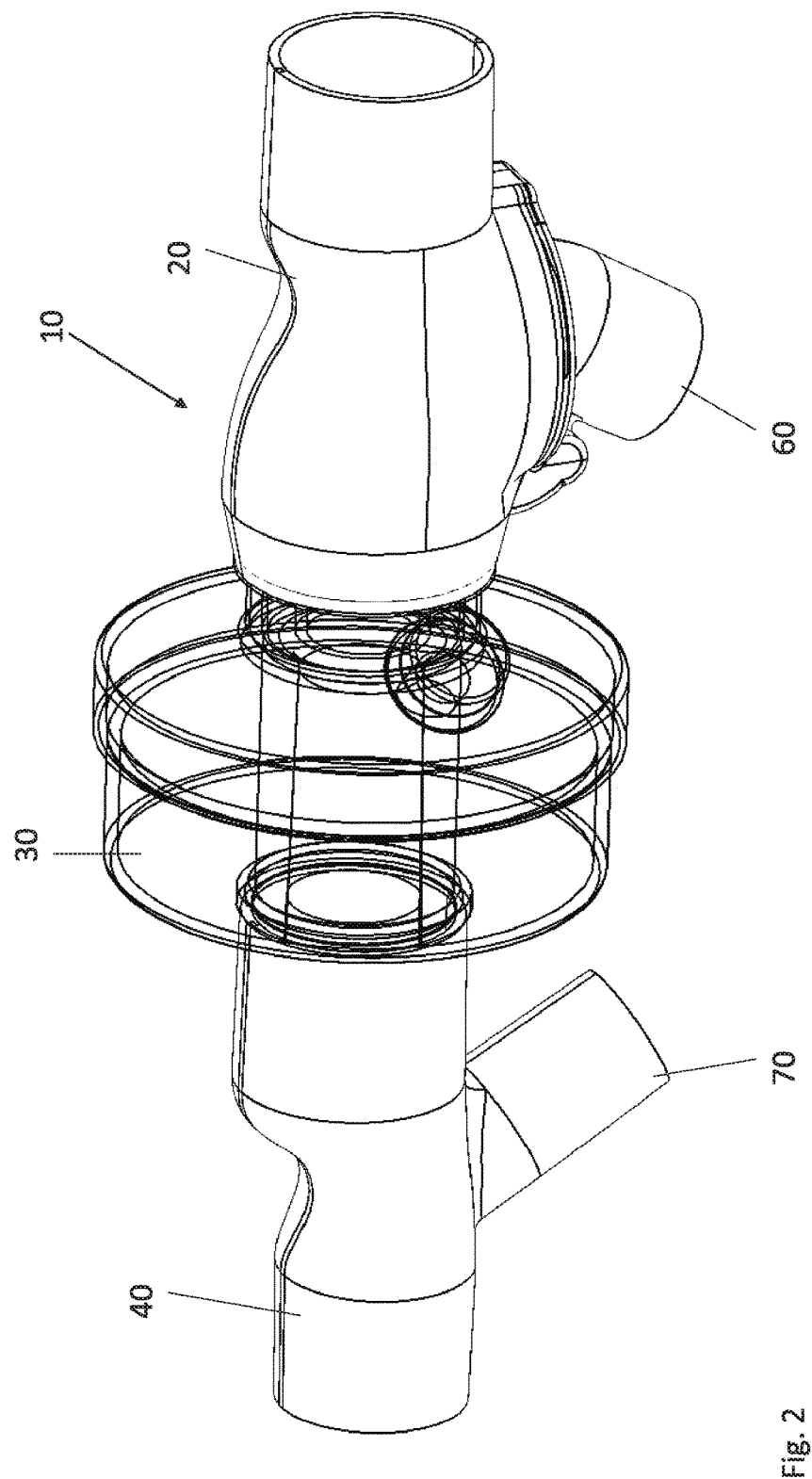
FIG. 2 is another perspective view of a bypass system of the present invention without a conduit connecting the first and second bypass conduits.

With reference to FIG. 2 and according to one embodiment of the present invention, the bypass system 10 is shown connected to a HME 30 without a conduit interconnecting first bypass conduit 20 and second bypass conduit 40. First bypass conduit 20 has a bypass channel 60 and second bypass conduit 40 has a bypass channel 70 which provides the bypass flow when the HME 30 is disconnected from first bypass conduit 20. The bypass channels 60 and 70 allow for a press fit with any conduits as would be commonly used within the respiratory field. The bypass channels 60 and 70 can be modified to assure a proper connection with any conduit as would be known by a worker skilled in the relevant art.

Figure 3:
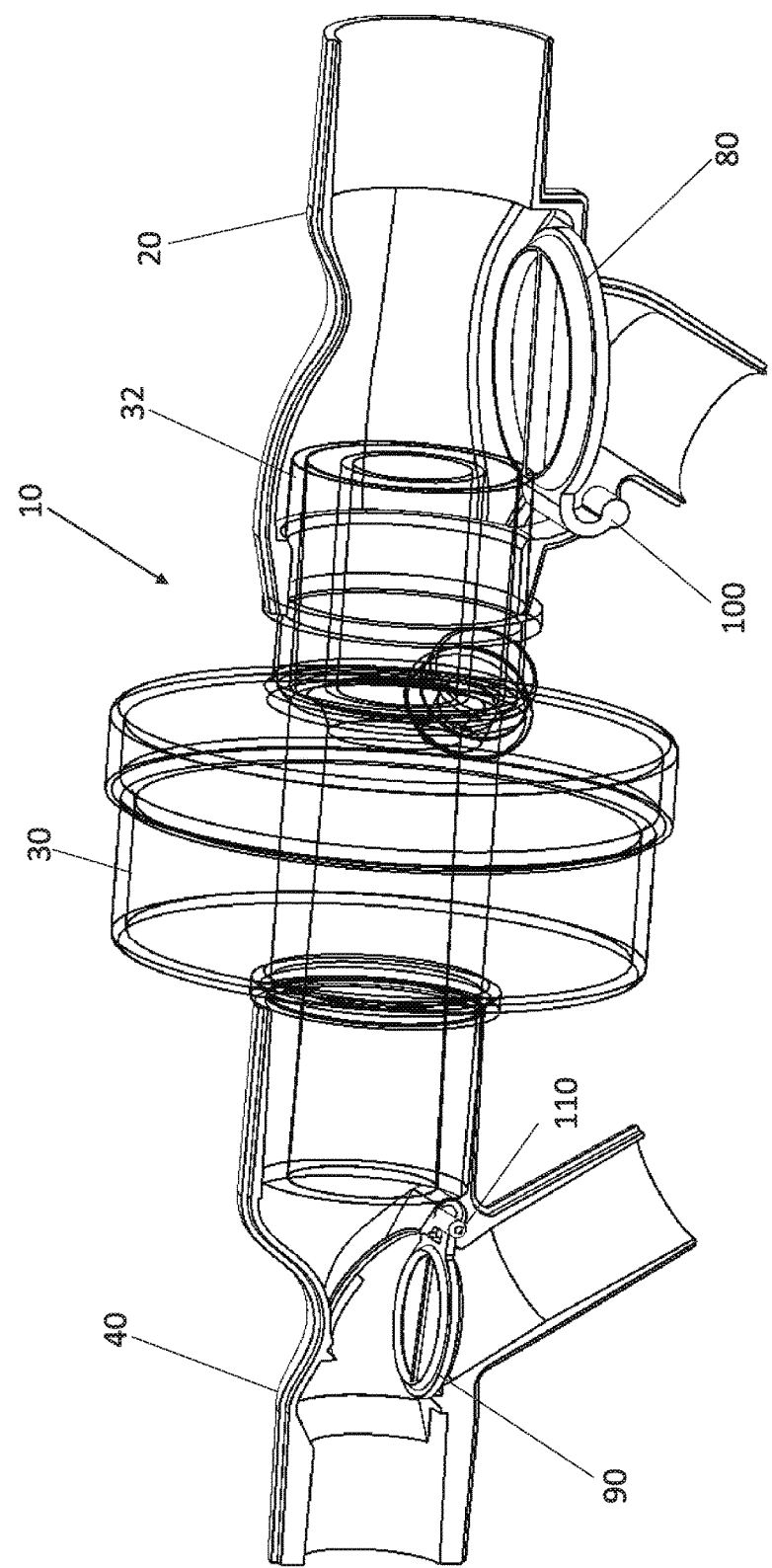
FIG. 3 is a cross-sectional view of the first and second bypass conduits connected to a heat and moisture exchanger.

With reference to FIG. 3 and according to one embodiment of the present invention, the first and second conduits 20 and 40 are shown in a cross sectional view which shows the first control valve 80 in the first bypass conduit 20 and a passive control valve 90 in second bypass conduit 40. The control valves 80 and 90 allow for the air flow to be diverted into a conduit (not shown) when the HME 30 is disconnected from first bypass conduit 20. With further reference to FIG. 3, the pivot point 100 of first control valve 80 is positioned nearest to the HME 30 allowing for movement of the first control valve 80 either away from the HME 30 or towards the HME 30. The pivot point 110 of passive control valve 90 is also positioned nearest to HME 30 within second bypass conduit 40 allowing for movement of the passive control valve 90. The pivot axis of each pivot points 100 and 110 is along the same axis wherein each pivot point is opposite to one another.

With reference to FIG. 4 and according to one embodiment of the present invention, the first bypass conduit 20 is shown disconnected from the HME 30. The second bypass conduit 40 is also disconnected from the HME 30. As can be appreciated, the first and second bypass conduits 20 and 40 are press fit onto the HME 30 allowing for ease of removal of the HME 30 from first and second bypass conduits 20 and 40. The ease of removal of the HME 30 from first and second bypass conduits 20 and 40 does not compromise the integrity of properly sealing out germs or bacteria. The HME aperture 24 on first conduit 20 is slid onto first conduit 32 of the HME 30 and aperture 42 on the second bypass conduit 40 is slid onto HME second conduit 34. A worker skilled in the relevant art would appreciate that apertures 24 and 42 on first and second conduit 20 and 40 can be inserted within the first and second HME conduits 32 and 34, respectively. The attachment method is based on the current industry accepted mechanism. In one embodiment the activation means is comprised of the first control valve 80 which is a pre-loaded elastomer valve with an internal seat on both sides. The pre-load ensures control valve 80 will close the aperture 24 automatically once the HME is removed. In another embodiment of the present invention, the activation means is comprised of a first control valve made from a spring loaded thermo-plastic valve as would be known by a worker skilled in the relevant art. The passive control valve 90 is a thermoplastic "swing valve" with an internal seat on both sides. In one embodiment, the range of movement of the passive control valve 90 is of 40 degrees allowing for opening and closing of the valve. The range of movement of the passive control valve 90 could be varied between 5 to 135 degrees based on some embodiments. In other embodiments and according to the present invention, the passive control valve is a silicone based control valve as would be known by a worker skilled in the relevant art. In another embodiment and according to the present invention, the passive control valve is a mechanically operated valve as would be known by a worker skilled in the relevant art.

With specific references to FIGS. 3 and 4 and according to one embodiment of the present invention, the first control valve 80 is pushed toward bypass channel 60 through the insertion of HME conduit 32 within aperture 24. Once HME conduit 32 is removed from aperture 24, the activation means in the form of the pre-loaded first control valve 80 will automatically move into an open position as shown in FIG. 4 allowing a diversion of air flow into bypass channel 60.

Figure 5B:
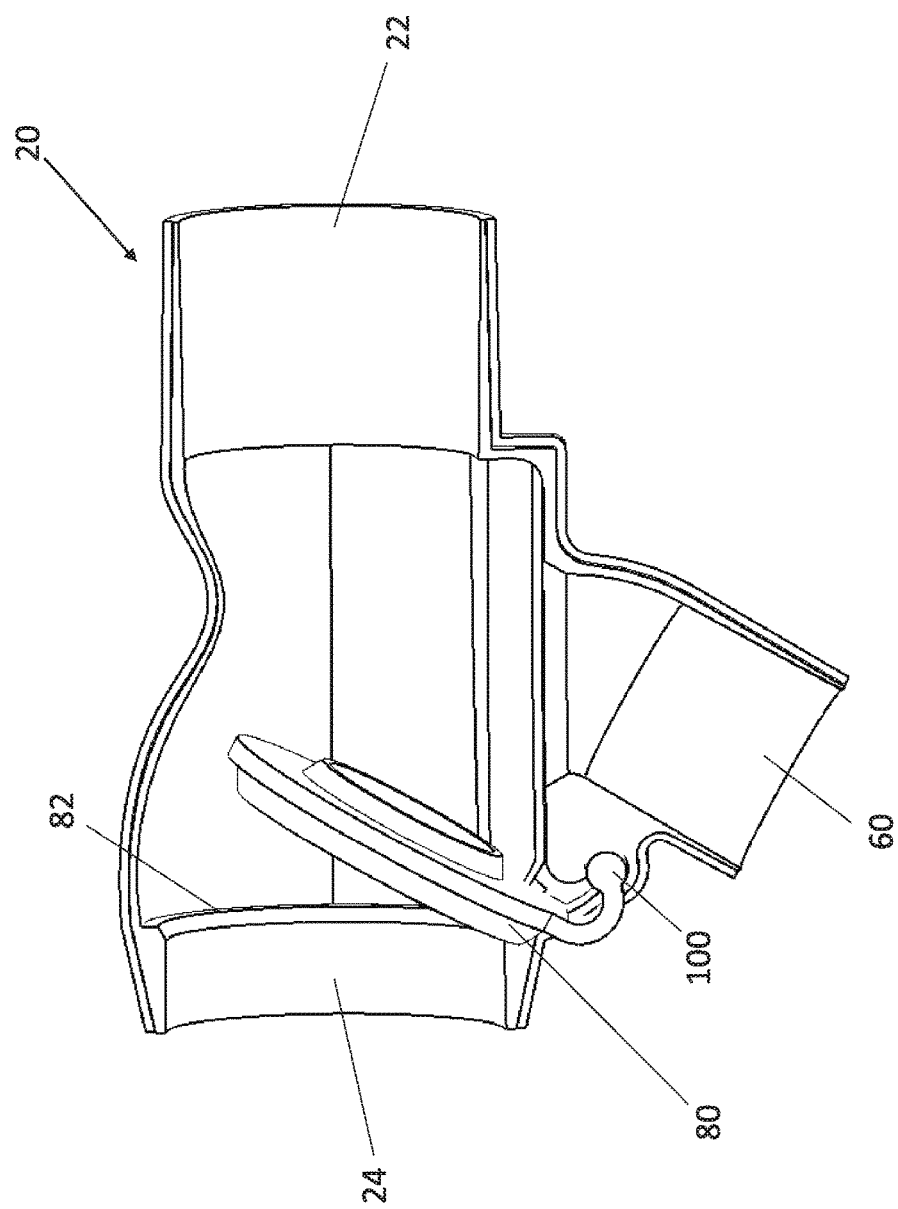
FIG. 5b is a vertical plane cross-sectional view of the first bypass conduit with a first control valve in a partial open position.

With reference to FIGS. 5a and 5b and according to one embodiment of the present invention, the first bypass conduit 20 is shown in greater detail. The first bypass conduit 20 has activation means comprised of a control valve 80 with a pivot point 100 allowing for movement of the control valve 80. The control valve 80 as shown in FIG. 5a represents the valve in a closed position which allows the movement of the air flow through the HME (not shown). The position of control valve 80 is in a closed position when the first conduit 20 is positioned on a HME (not shown). With reference to FIG. 5b and according to one embodiment of the present invention, the control valve 80 is shown in a partially open position representing that the first bypass section 20 is not connected to an HME (not shown). The activation means consisting of the first control valve 80 will automatically open when a first bypass conduit 20 is removed from an HME (not shown). The first control valve 80 will not remain in a partially closed position at no time when an HME (not shown) is removed from a first bypass conduit 20. With further reference to FIG. 5b, the control valve 80 pivots on pivot point 100 and meshes with lip 82 providing a sealing connection and redirecting the air flow into bypass channel 60. When the control valve 80 is in an open position, the first control valve 80 also seals with lip 82 in order to provide a sealing connection and allowing air to flow through bypass channel 60. The first control valve 80 and lip 82 are designed to provide an airtight seal since otherwise bacteria or germs could enter the air flow to the patient. A worker skilled in the relevant art would be familiar with numerous applications which can provide a sealing connection between a lip and a valve as shown in FIGS. 5a and 5b.

Figure 6A:
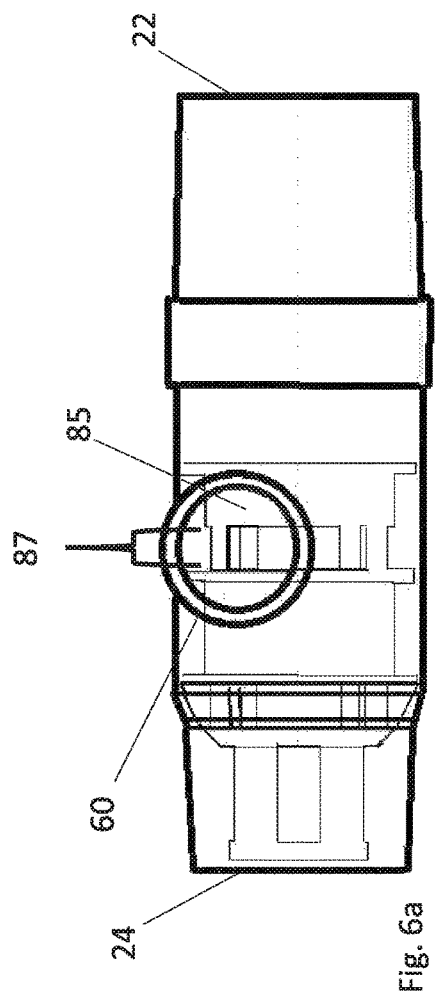
FIG. 6a is a translucent profile view of the first bypass conduit with an actuating piston in an open position allowing for a passage of gas into a conduit.
Figure 6B:
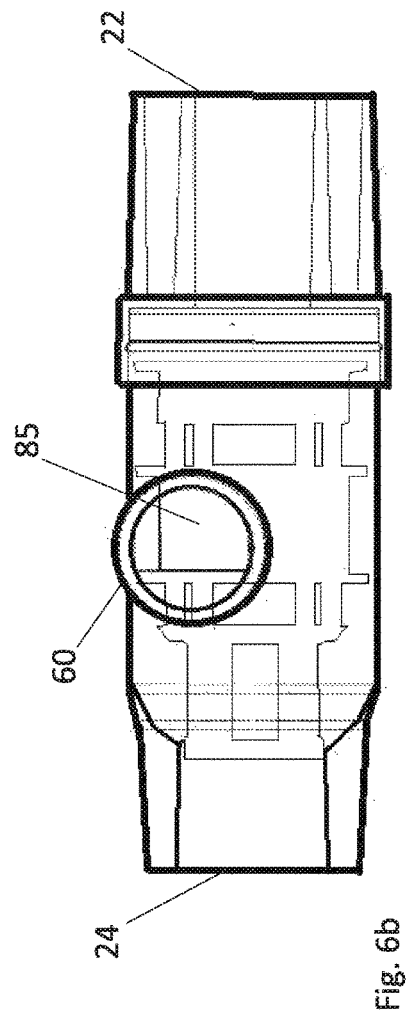
FIG. 6b is a translucent profile view of the first bypass conduit with an actuating piston in a closed position allowing for a passage of gas into a filtration device.

With reference to FIGS. 6a and 6b and according to another embodiment of the present invention, the first bypass conduit 20 containing an actuating piston 85 is shown in greater detail. In this embodiment, the second conduit (not shown) remains the same as in the first embodiment which includes a passive valve and is not further described. In another embodiment and according to the present invention, the activation means is comprised of an actuating piston 85 which opens or closes the bypass channel 60, depending on the presence or absence of the HME (not shown). With specific reference to FIG. 6a, the bypass conduit 20 is shown in the absence of the HME (not shown). In the absence of the HME (not shown) the actuating piston 85 is positioned by aperture 24 by a spring mechanism (not shown). When positioned by aperture 24, the air vent 87 of the actuating piston 85 is located at the bypass channel 60, thereby permitting air to travel through the conduit (not shown) and not through aperture 24 which would be connected to an HME not shown. With specific reference to FIG. 6b, the bypass conduit 20 is shown in the presence of the HME (not shown) positioned on aperture 24. The HME (not shown) when inserted onto the bypass conduit 20 displaces the actuating piston 85 from its resting location, at aperture 24, and pushes it into the center of the bypass conduit 20. A centrally located actuating piston 85 relocates the air vent 87 away from the bypass channel 60, thereby prohibiting the air to travel through the conduit (not shown) and thereby allowing the air to travel to the HME (not shown). The use of a actuating piston would be based on the knowledge of a worker skilled in the relevant art.

Figure 7:
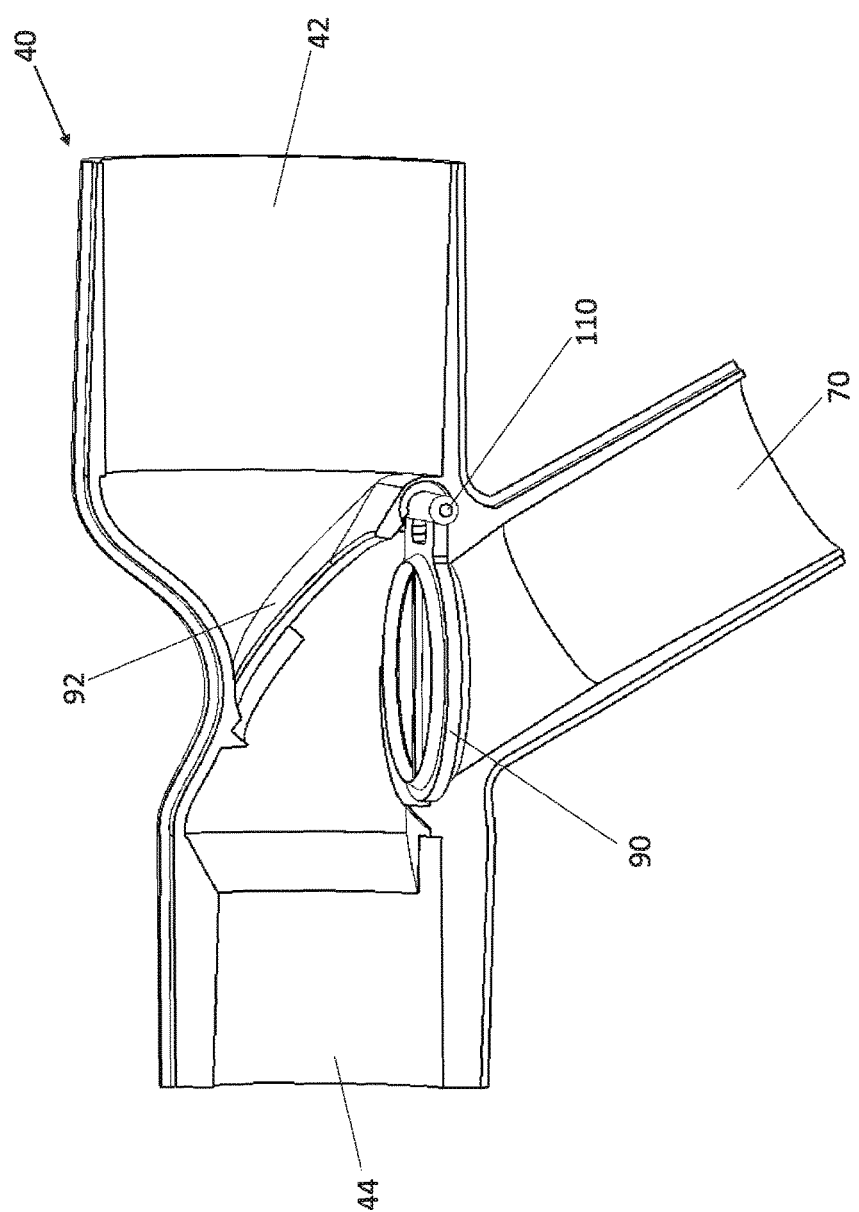
FIG. 7 is a vertical plane cross-sectional view of the second bypass conduit with a second control valve in a closed position.
Figure 8:
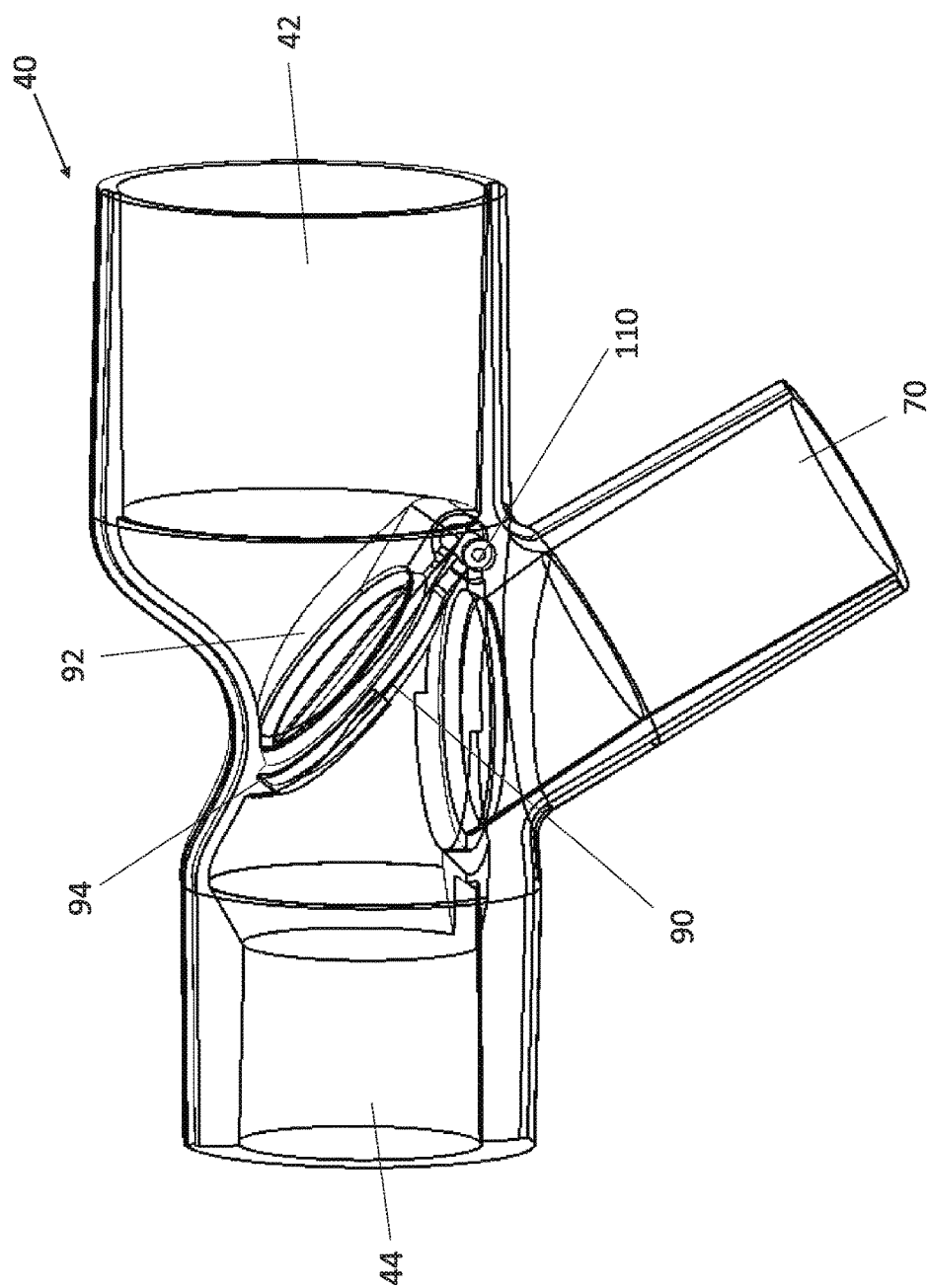
FIG. 8 is a vertical plane cross-sectional view of the second bypass conduit with a second control valve in an open position.

With reference to FIGS. 7 and 8 and according to one embodiment of the present invention, the second bypass conduit 40 is shown is greater detail having aperture 44. The passive control valve 90 pivots on pivot point 110 and is shown in a closed position in FIG. 7. When the passive control valve 90 is in a closed position, the air flow passes through an HME (not shown) before passing through the second bypass conduit 40. With reference to FIG. 8, the passive control valve 90 is shown in an open position representing that the second bypass conduit 40 is not connected to an HME (not shown). The movement of passive control valve 90 into an open position will also occur when first bypass conduit (not shown) is disconnected from an HME (not shown). When the passive control valve 90 is in an open position, the passive control valve 90 also seals with lip 92 in order to provide a sealing connection and allowing air to flow through bypass channel 70. The passive control valve 90 and lip 92 are designed to provide an airtight seal since otherwise bacteria or germs could enter the air flow to the patient. Lip 92 also has a backflow valve protection ridge 94, to prevent the lifting of the valve in the presence of backflow. A worker skilled in the relevant art would be familiar with numerous applications which can provide a sealing connection between a lip and a valve as shown in FIGS. 7 and 8. In one embodiment of the present invention, the passive control valve is automatically activated open the first control valve being in an open position through the activation means.

Figure 9:
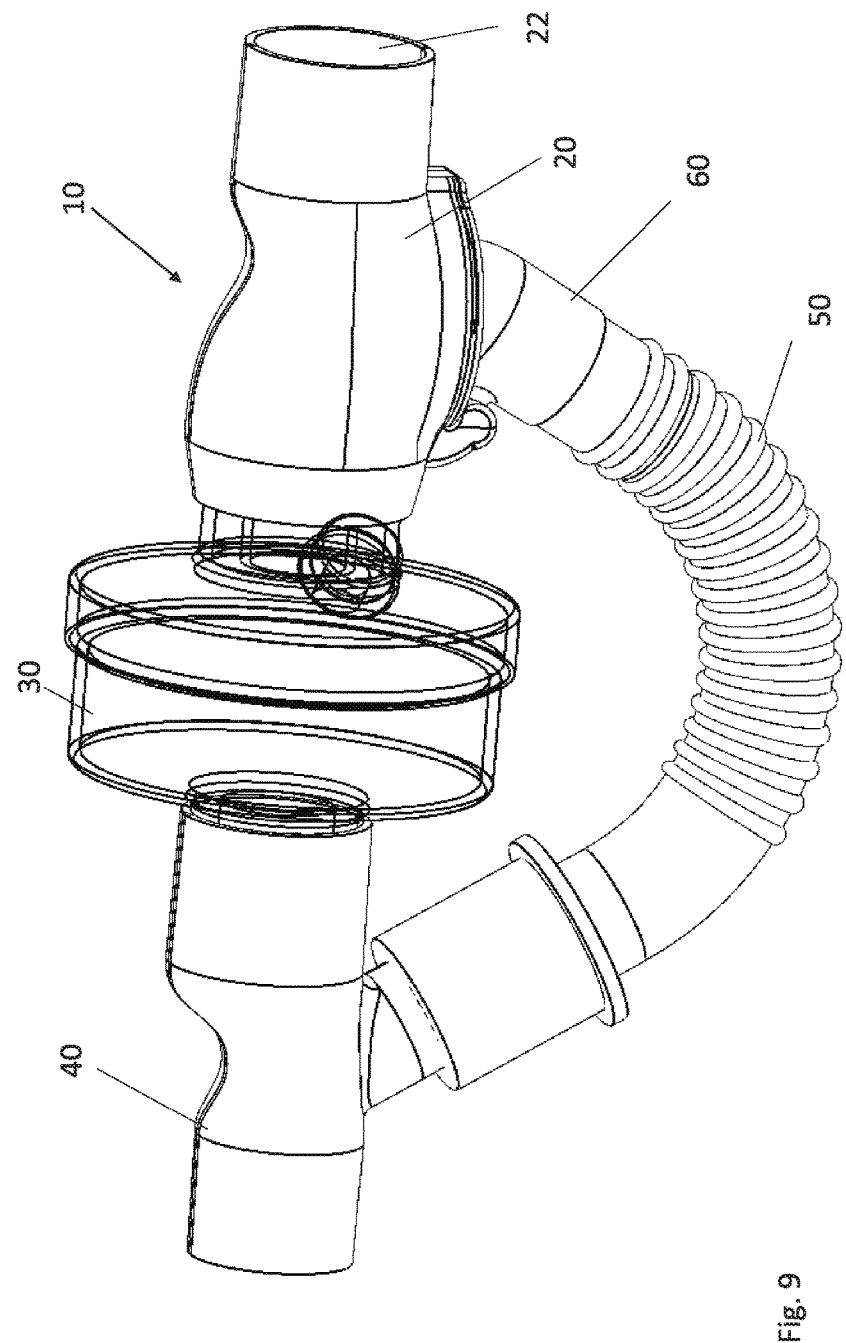
FIG. 9 is a perspective view of the bypass system positioned on a heat and moisture exchanger according to one embodiment of the present invention.

With reference to FIG. 9, the bypass system 10 is shown connected to a HME 30 according to one embodiment of the present invention. In operation, the first bypass conduit 20 is connected at one end of the HME 30 and the second bypass conduit 40 is attached to the opposite end of the HME 30. A standard metered dose inhaler or nebulizer tee, as would be found in this field of respiratory therapy and anesthesia can be added between the bypass channel 60 and conduit 50. When the HME is removed and the gas flow follows the pattern described below, such a diversion of the gas flow allows a healthcare provider to administer inhaled medications through conduit 50 thus avoiding the HME media. The conduit 50 is also connected to the first conduit 20 and second bypass conduit 40 allowing for the flow of air to be diverted when the HME 30 is removed from the system and as detailed below.

Figure 10:
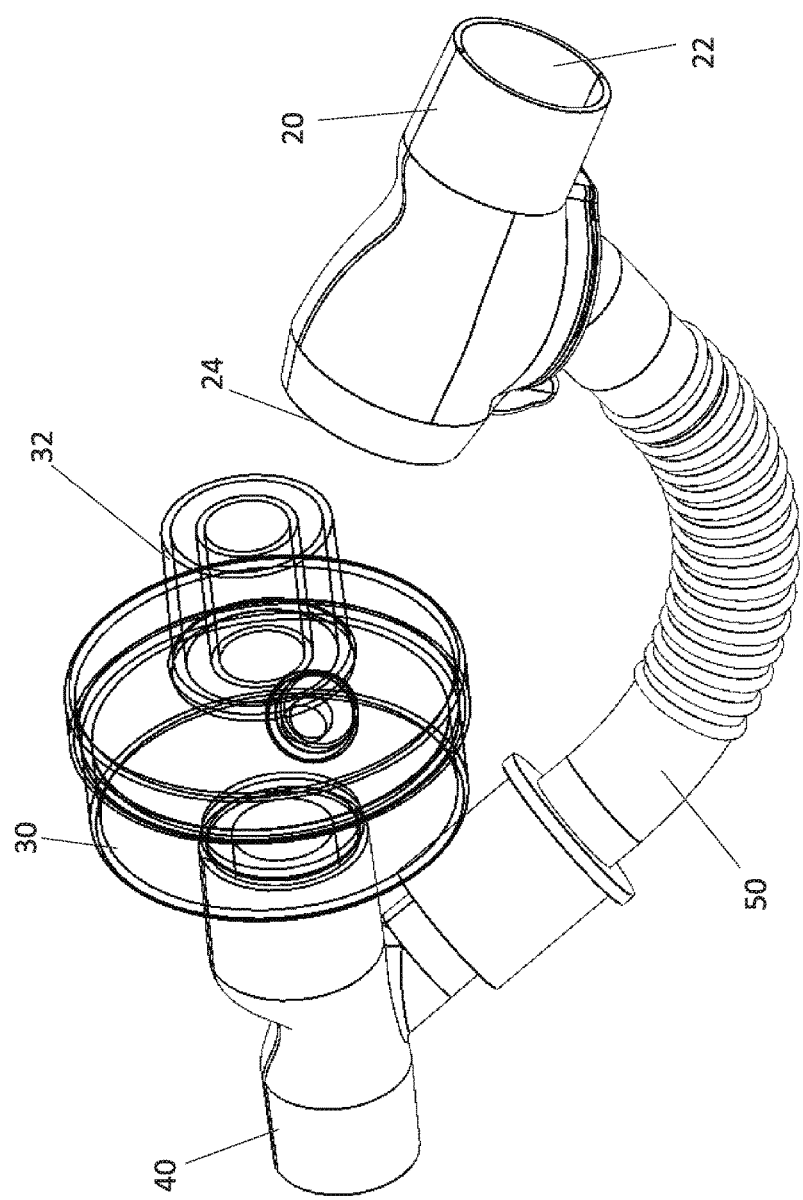
FIG. 10 is a perspective view of the first bypass conduit removed from the heat and moisture exchanger according to one embodiment of the present invention.

With reference to FIG. 10 and according to one embodiment of the present invention, the first bypass conduit 20 is detached from the HME 30 and specifically aperture 24 of first bypass conduit 20 is removed from the HME conduit 32. With the removal of first bypass conduit 20 from the HME 30, through the activation means the first control valve (not shown) is moved from a closed position to an open position. The movement of first control valve (not shown) is achieved through the first control valve being a pre-loaded elastomer valve, with the pre-load directed towards aperture 24. The insertion of HME conduit 32 into aperture 24 positions (pushes and maintains) the first control valve into a closed position allowing for air to travel through the HME 30. When the HME 30 is disconnected from the first bypass conduit 20 the pre-loaded elastomer control valve 80 (not shown) opens to the bypass channel 60 (not shown) and closes aperture 24. This redirection of the flow (and pressure) in turn causes a drop in the pressure present in the HME 30 to atmosphere and increases the pressure within the bypass conduit thus activating the passive control valve 90 (swing valve—not shown) to bypass the flow within conduit 50. The pressure within a respiratory or anesthesia treatment system is automatically at a higher pressure than normal atmospheric pressure creating the movement of passive control valve 90 when the HME 30 is disconnected. Such a pressure differential allows for the automatic movement of the passive control valve 90 without the need for any action by a care giver. The activation means consisting of the pre-loaded control valve 80 also allows for an automatic movement of the first control valve without any manual operation required by a care giver when the HME 30 is disconnected from the first bypass conduit 20.

Figure 11:
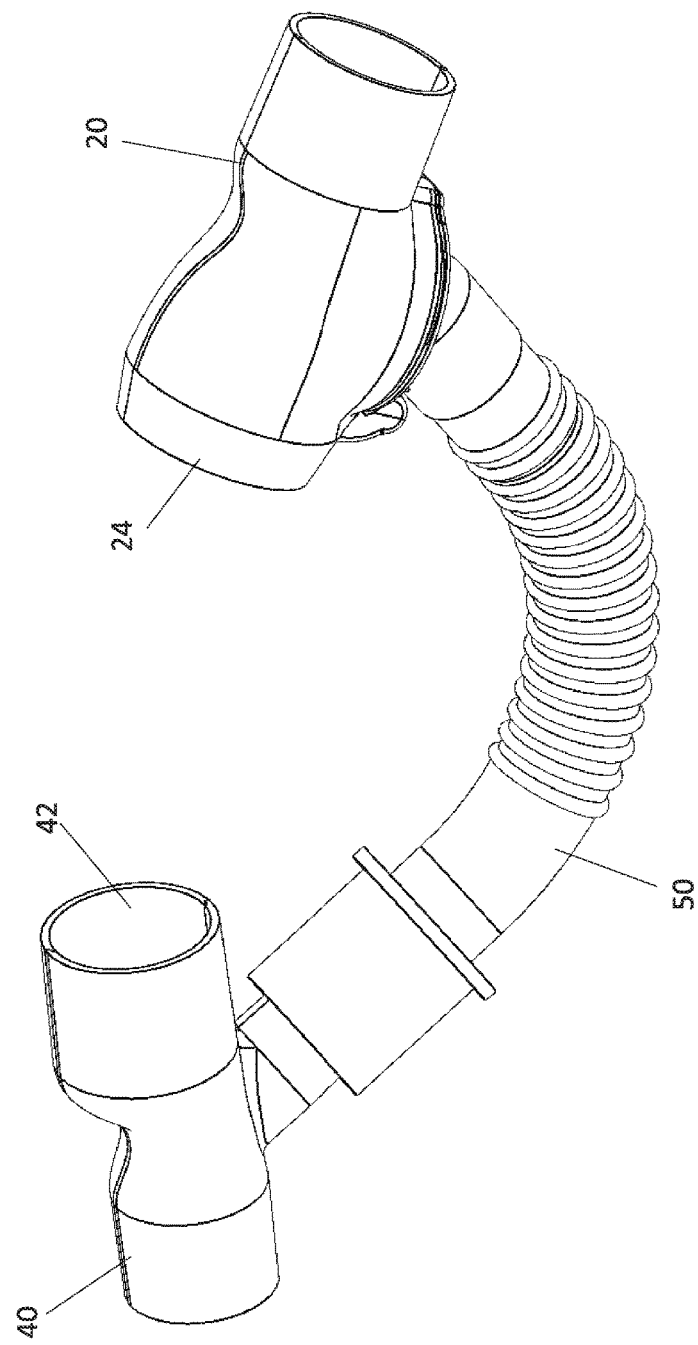
FIG. 11 is a perspective view of the bypass system without a heat and moisture exchanger connecting the first and second bypass conduits according to one embodiment of the present invention.

With further reference to FIGS. 10 and 11 and according to one embodiment of the present invention, with the activation of the first control valve 80 (not shown), the air flow is then diverted into the conduit 50 which results in the movement of the passive control valve 90 from a closed positioned to an open position allowing for the entire removal of the HME 30 without interrupting the flow of air to a patient. With reference to FIG. 10 and according to one embodiment of the present invention, the bypass system allows for a continuous flow of oxygen/air while either replacement or maintenance is conducted on an HME or any other unit that could be used in respiratory therapy. This also does not require any manual or specific operation by a caregiver in moving the first control valve and passive valve.

With further reference to FIG. 10 and according to one embodiment of the present invention, with the activation of the first control valve 80 (not shown), the air flow is then diverted into the conduit 50 which results in the movement of the passive control valve 90 from a closed positioned to an open position such that the first conduit aperture 24 is closed without interrupting the flow of air to a patient. When in this state, a healthcare professional may attach a manual resuscitation bag or transport ventilator, as would be found in this field of respiratory therapy or anesthesia to HME conduit 32. At this time the fixed ventilator circuit can be disconnected from aperture 22 on the first control valve which will cause the second bypass conduit 40 to close second control valve (not shown) and allow the airflow from the manual/transport ventilator to travel through the HME to the patient thus ensuring at all times that the flow of air/oxygen was never interrupted and did not require any specific manual application or operation by a caregiver to move the first control valve and the passive control valve.

Figure 12:
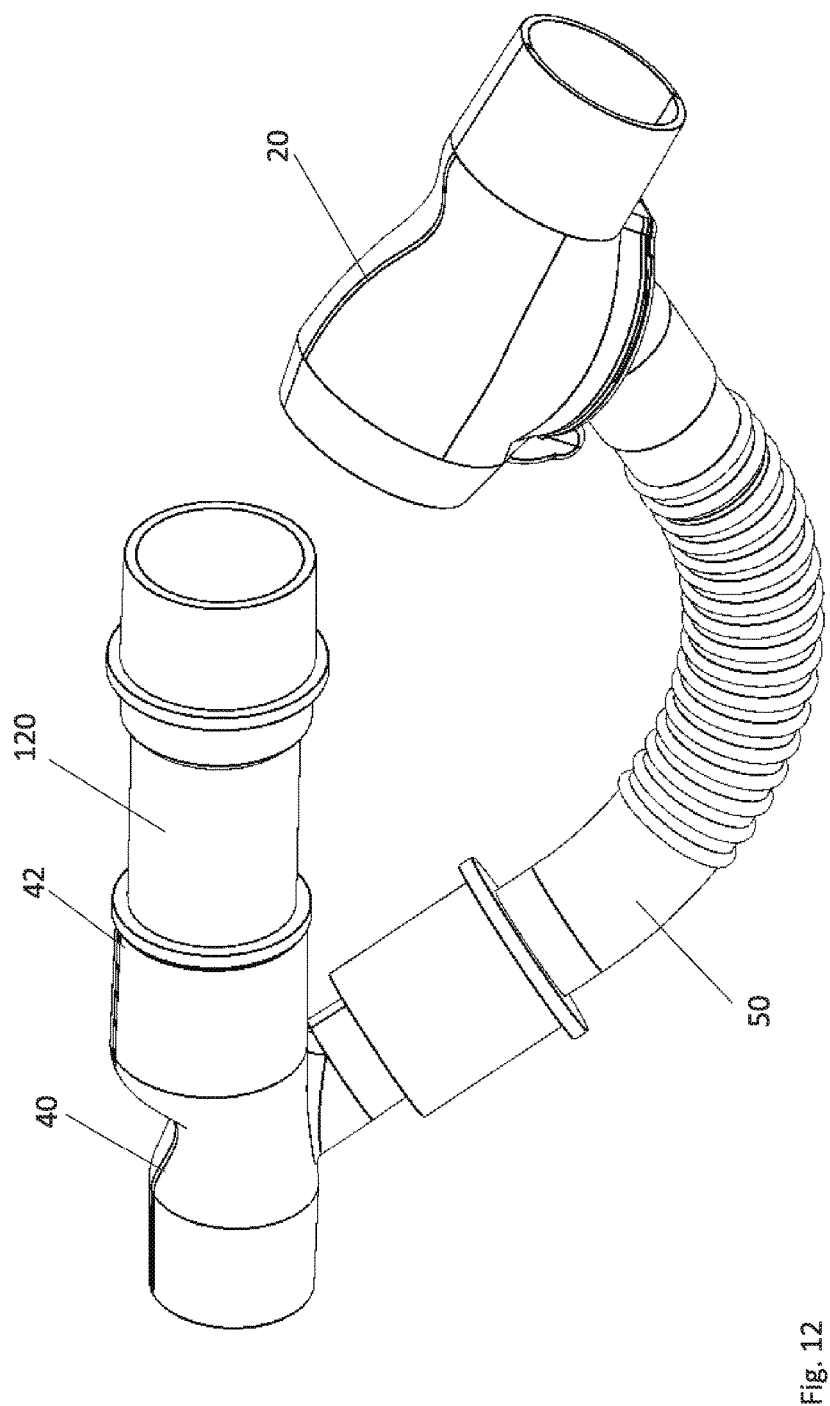
FIG. 12 is a perspective view of a connecting conduit installed on the second bypass conduit according to one embodiment of the present invention.

With reference to FIG. 12 and according to one embodiment of the present invention, a connecting conduit 120 is connected to aperture 42 of the second bypass conduit 40. When the connecting conduit 120 is only connected to aperture 42, the first control valve and passive control valve (not shown) remain in an open position maintaining the air flow through conduit 50.

Figure 13:
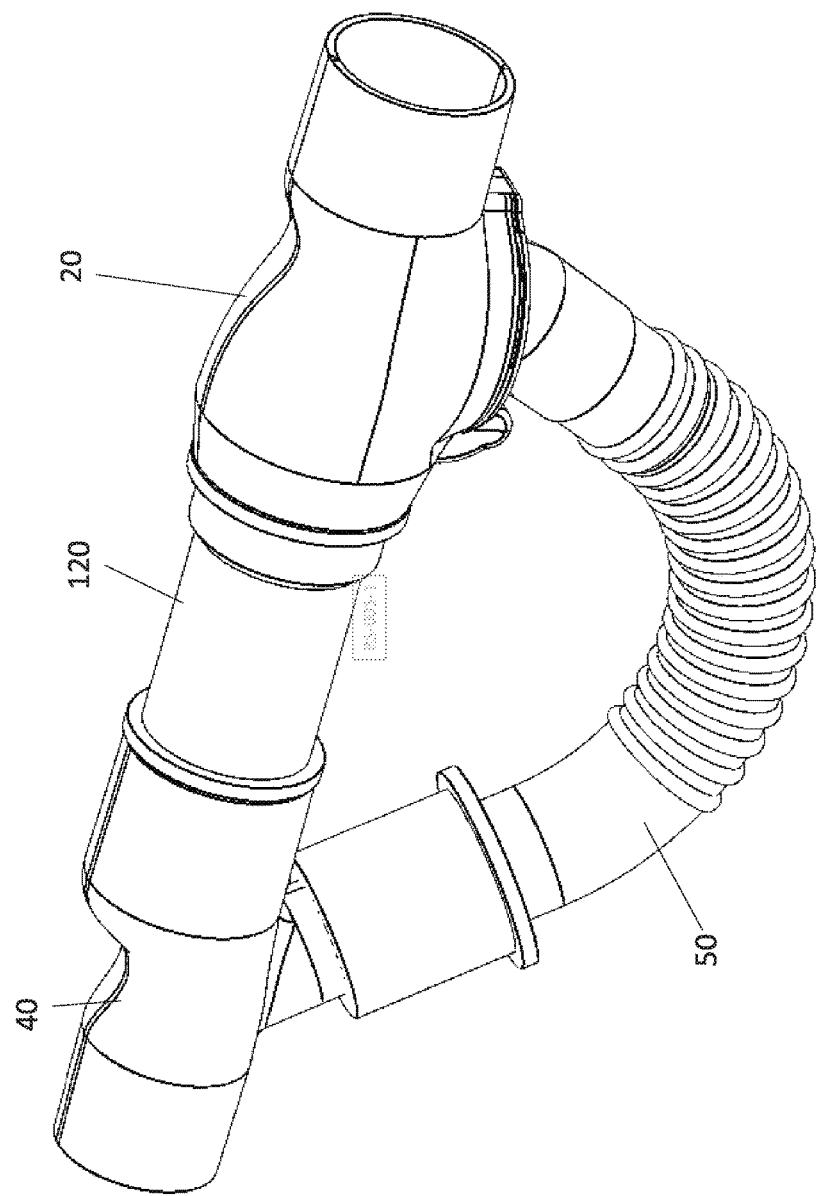
FIG. 13 is a perspective view of the bypass system having a connecting conduit according to one embodiment of the present invention.

With reference to FIG. 13 and according to one embodiment of the present invention, the connecting conduit 120 is connected to the first and second bypass conduits 20 and 40 which results in the activation means to move the first control valve and passive control valve (not shown) to move from an open position to a closed position. The air flow is then diverted from conduit 50 to the connecting conduit 120. The use of conduit 120 is ideal when mechanically ventilating a patient using an active humidity system (a heater incorporated with a heated wire circuit). An active humidity system would be used in place of an HME as would be found in this field of respiratory therapy and as would be known by a worker skilled in the relevant art.

A method is also provided under the present invention in order to allow for the removal of an HME without interrupting the flow of gases from a respiratory or anesthesia treatment system. With further reference to FIG. 10, the first step requires the removal of first bypass conduit 20 from the a filtration device and in this case a HME 30. Through this first step, the activation means will open first control valve (not shown) closing aperture 24 through the pre-loading characteristics of the first control valve which is the activation means. The second step requires the removal of second bypass conduit 40 from HME 30. The sequence of these two steps is important since otherwise control valves found in both first and second bypass conduits 20 and 40 will not automatically activate allowing for an uninterrupted flow of gases within the system. With further reference to FIG. 12, a third step in this method would be the installation of a connecting conduit 120 through the installation of the connecting conduit 120 on aperture 42 of the second bypass conduit 40. A fourth step in this method would be installing connecting conduit 120 into aperture 24 of the first bypass conduit 20. Steps 3 and 4 are optional steps and are only required in order to activate the bypass system for use with active humidity systems.

A method for bypassing air flow for use in respiratory therapy and anesthesia comprising the steps of:

a) providing an air flow passage to a patient for assistance in artificial ventilation having an air flow passage;

b) disconnecting a first bypass conduit from the air flow passage; and c) diverting the air flow into a conduit interconnecting the first bypass conduit and a second bypass conduit.

The present invention may be used in combination with artificial ventilation systems having an HME, active humidity system, a ventilator or a manual resuscitation bag manual as would be used by a qualified health provider. The installation of the present system within an artificial ventilation system requires the first and second bypass conduits to be in a direct connection with an HME, ventilator or manual resuscitation bag.

A person understanding this invention may now conceive of alternative structures and embodiments or variations of the above all of which are intended to fall within the scope of the invention as defined in the claims that follow.

A bypass system for respiratory therapy and anesthesia comprising: a) a first bypass conduit for receiving a gas flow and for receiving a filtration device; b) an activation means for redirecting the gas flow within the first bypass conduit; c) a second bypass conduit for receiving the gas flow from the first bypass conduit and the filtration device; d) a passive control valve within the second bypass conduit to redirect air flow within the second bypass conduit; e) a conduit interconnected to the first and second bypass conduit for providing a passage of gases between the first and second bypass conduit when activated by the activation means; and, wherein the activation means is activated when the first bypass conduit is not connected to a filtration device.

I claim:

1. A bypass system for respiratory therapy and anaesthesia comprising:

a) a first bypass conduit for receiving a gas flow and for receiving a filtration device;

b) an activation device for redirecting the gas flow within the first bypass conduit, the activation device moveable between an open position and a closed position;

c) a second bypass conduit for receiving the gas flow from the first bypass conduit and the filtration device;

d) a passive control valve moveable between a first position and a second position in response to a corresponding position of the activation device, the passive control valve located within the second bypass conduit to redirect air flow within the second bypass conduit;

e) a conduit interconnected to the first and second bypass conduit for providing a passage of gases between the first and second bypass conduit when activated by the activation device; and, wherein the activation device is activated when the first bypass conduit is not connected to the filtration device; and, wherein a pressure differential is created when the activation device is moved between the open position and the closed position, and the pressure differential a correspondingly moves the passive control valve from the first position to the second position.

2. The bypass system according to claim 1, wherein the activation device is comprised of a preloaded elastomer valve.

3. The bypass system according to claim 1, wherein the activation device is comprised of a spring loaded thermoplastic valve.

4. The bypass system according to claim 1, wherein the activation device is comprised of an actuating piston.

5. The bypass system according to claim 1, wherein the filtration device is a heat and moisture exchanger.

6. The bypass system according to claim 1, wherein the filtration device is a connecting conduit.

7. The bypass system according to claim 1, wherein the passive control valve is a silicone based compound.

8. The bypass system according to claim 1, wherein the passive control valve is a thermo-plastic valve.

9. A method for bypassing air flow for use in respiratory therapy and anaesthesia comprising the steps of:

a) providing an air flow passage to a patient for assistance in artificial ventilation having an air flow passage;

b) disconnecting a first bypass conduit from the air flow passage which activates a passive control valve within a second bypass conduit, the passive control valve moveable between a first position and a second position; and c) diverting the air flow into a conduit interconnecting the first bypass conduit and the second bypass conduit, wherein the disconnection of the first bypass conduit from the air flow passage increases a gas flow pressure in the first bypass conduit, thereby moving the passive control valve from the first position to the second position.

* * * * *